US008436617B2

(12) United States Patent  (10) Patent No.: US 8,436,617 B2
Renz et al.                  (45) Date of Patent:     May 7, 2013

(54) COMPENSATION DEVICE TO REDUCE THE ELECTROMAGNETIC FIELD LOAD DUE TO A MEDICAL INTERVENTION APPARATUS IN MAGNETIC RESONANCE EXAMINATIONS

(75) Inventors: Wolfgang Renz, Erlangen (DE); Anke Weissenborn, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 456 days.

(21) Appl. No.: 12/698,282

(22) Filed: Feb. 2, 2010

(65) Prior Publication Data
US 2010/0194391 A1  Aug. 5, 2010

(30) Foreign Application Priority Data
Feb. 2, 2009 (DE) .......................... 10 2009 007 044

(51) Int. Cl.
G01V 3/00 (2006.01)
G01R 33/20 (2006.01)
A61B 5/05 (2006.01)

(52) U.S. Cl.
USPC ............................ 324/322; 324/318; 600/411

(58) Field of Classification Search .......... 324/300–322; 600/600–407; 382/128–131
See application file for complete search history.

(56) References Cited

U.S. PATENT DOCUMENTS

| | | | | |
|---|---|---|---|---|
| 2,288,838 A * | 7/1942 | Pike et al. | ........................ | 73/658 |
| 2,615,129 A * | 10/1952 | McMillan | ...................... | 315/502 |
| 2,756,383 A * | 7/1956 | Nold et al. | ..................... | 324/301 |
| 2,948,845 A * | 8/1960 | Handel | .......................... | 324/319 |
| 2,964,696 A * | 12/1960 | Pinkley | ......................... | 324/322 |
| 2,978,649 A * | 4/1961 | Weiss | .............................. | 307/424 |
| 3,099,793 A * | 7/1963 | Pinkley | ......................... | 324/313 |
| 3,153,201 A * | 10/1964 | Knight | .......................... | 324/322 |
| 3,204,020 A * | 8/1965 | Michel | ............................ | 84/695 |
| 3,284,700 A * | 11/1966 | Kingston | ...................... | 324/308 |
| 3,430,128 A * | 2/1969 | Lovins | .......................... | 324/322 |
| 3,443,150 A * | 5/1969 | Staats | ........................ | 315/39.51 |
| 3,502,963 A * | 3/1970 | Hlavka | .......................... | 324/310 |
| 3,525,931 A * | 8/1970 | Aisenberg | ..................... | 324/204 |
| 6,977,503 B2 * | 12/2005 | Prado | ............................ | 324/319 |
| 7,358,737 B2 * | 4/2008 | Hoult | ............................. | 324/322 |
| 8,073,551 B2 * | 12/2011 | McCann et al. | ............. | 607/101 |
| 8,168,120 B1 * | 5/2012 | Younis | ....................... | 422/82.01 |
| 2004/0155659 A1 * | 8/2004 | Prado | ............................ | 324/322 |
| 2007/0222449 A1 * | 9/2007 | Hoult | ............................. | 324/318 |
| 2007/0270924 A1 * | 11/2007 | McCann et al. | ................ | 607/99 |
| 2008/0058913 A1 | 3/2008 | Gray et al. | ................... | 607/116 |
| 2010/0160997 A1 * | 6/2010 | Johnson et al. | ................. | 607/45 |
| 2010/0194391 A1 * | 8/2010 | Renz et al. | .................... | 324/314 |

* cited by examiner

*Primary Examiner* — Melissa Koval
*Assistant Examiner* — Tiffany Fetzner
(74) *Attorney, Agent, or Firm* — Schiff Hardin LLP

(57) ABSTRACT

A compensation device to reduce the electromagnetic field load due to the presence of a medical intervention apparatus in magnetic resonance examinations, has: a control device that has a radio-frequency input and a radio-frequency output, an injection device that is connected with the radio-frequency output and that injects the radio-frequency power delivered by the control device into the medical intervention apparatus, a measurement device that measures at least one electrical variable at the intervention apparatus, and a regulator that is connected with the control device and the measurement device. The regulator adjusts the control device to deliver the radio-frequency power so that the electrical variable at the intervention apparatus is reduced.

12 Claims, 1 Drawing Sheet

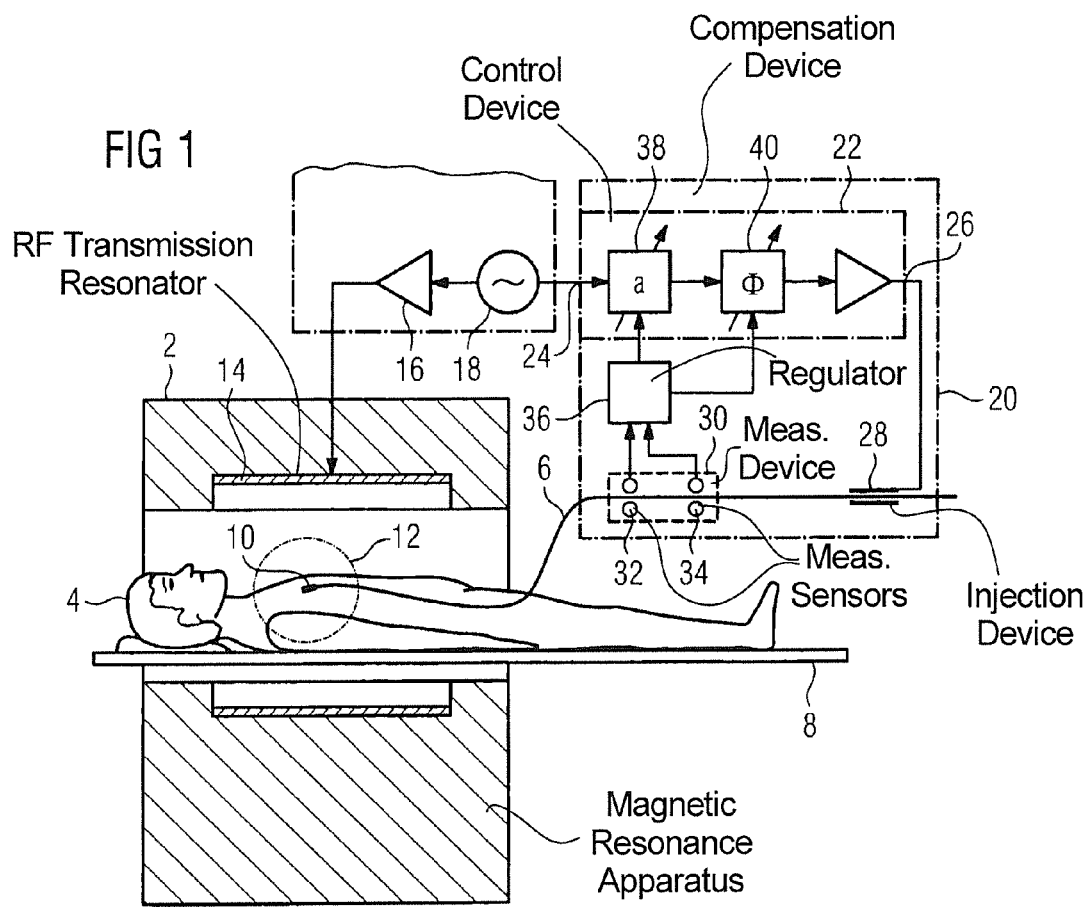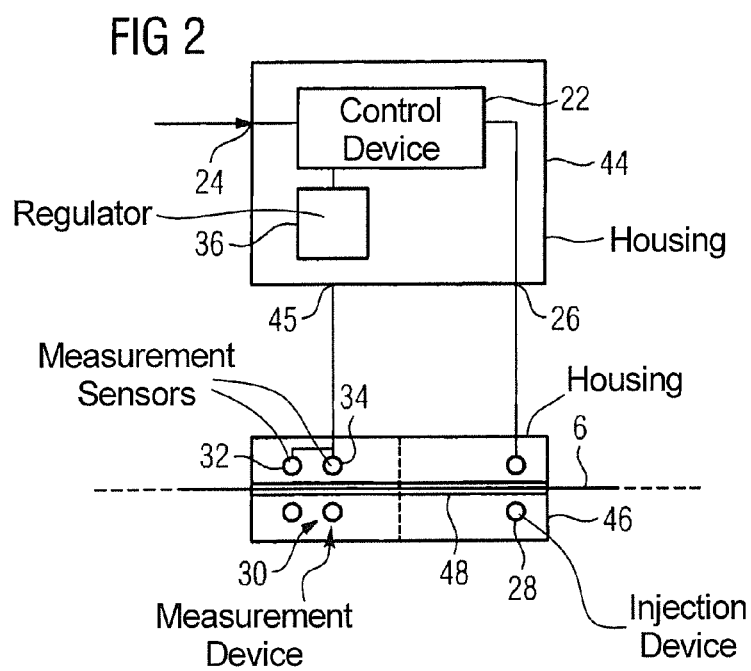

COMPENSATION DEVICE TO REDUCE THE ELECTROMAGNETIC FIELD LOAD DUE TO A MEDICAL INTERVENTION APPARATUS IN MAGNETIC RESONANCE EXAMINATIONS

BACKGROUND OF THE INVENTION

1. Field of the Invention

The present invention concerns a device to reduce the electromagnetic field load caused by the presence of a medical intervention apparatus in magnetic resonance examinations.

2. Description of the Prior Art

Many medical procedures today are conducted in an interventional manner. Diagnostic or therapy methods that—in contrast to conservative procedures—conduct targeted procedures (interventions) on pathological tissue in order to positively affect the course of the illness are designated as interventional. Invasive or, respectively, minimally invasive procedures are also examples of such methods, wherein medical instruments or implants are brought to the treatment or examination location by various techniques.

Particularly in the treatment of vascular diseases, guide wires are used that are inserted by a physician into hollow vessels (lumens) of a patient. Later a catheter (for example) is inserted along this wire for diagnosis or therapy. The guide wire itself often has a diameter of less than 0.5 mm. Due to the high mechanical demands, such guide wires have been conventionally produced from metal and metal alloys. Magnetic resonance is a modality particularly suited for imaging of the human body with a high tissue contrast. It would be particularly suitable for observation of intervention apparatuses during their insertion and placement in the human body, but the electromagnetic fields in the two-digit or three-digit megahertz range that are required for imaging are problematical. Therefore, heretofore there have been high risks in the real-time tracking of guide wires and other electrically conductive intervention apparatuses given movement in the human body. This is highly risky because high-frequency currents can form on elongated electrically conductive apparatuses due to injection of the transmission fields. This leads to heating at corresponding powers and, in the disadvantageous case, to tissue burns inside the human body. The currents are even higher at such elongated intervention apparatuses if waveguide resonances occur along the entire length due to the intervention apparatus. If the lengths of the guide wires are also on the order of the wavelength of the magnetic resonance frequencies being used, the risk of endangering a patient is particularly high.

A prediction about the potential for danger by means of simulation calculations is very difficult since the actual danger is situation-dependent. The length and orientation of the intervention apparatus in the patient, the conductive paths outside the patient, and even properties of the patient, play a role. Finally, the position of the intervention apparatus in relation to the transmission antenna, and the transmission antenna type, are also very influential.

Due to the high risks from the induced radio-frequency currents, the real-time tracking of intervention apparatuses with the aid of magnetic resonance has previously been realized with the transmission power being drastically limited. Another solution is the construction of guide wires or catheters from non-conductive materials. However, all desired material properties cannot be ensured with these materials; such intervention apparatuses are additionally very expensive and complicated.

SUMMARY OF THE INVENTION

An object of the present invention is to provide a device with which the electrical field load due to a medical intervention apparatus can be reduced in magnetic resonance examinations.

The object is achieved according to the invention by a magnetic resonance device having a control device that has a radio-frequency input and a radio-frequency output, an injection device that is connected with the radio-frequency output and is fashioned to inject the radio-frequency power delivered by the control device into the medical intervention apparatus, a measurement device that measures at least one electrical variable at the intervention apparatus, and a regulator that is connected with the control device and the measurement device, the regulator being configured to adjust the control device to deliver the radio-frequency power so that the electrical variable at the intervention apparatus is reduced. Use is made of the fact that the intervention apparatus represents an only weakly damped radio-frequency wave guide in which the current flows (paths) repeat periodically. The current flow at the patient-proximal end of the intervention apparatus therefore can be detected at least approximately by a measurement at the patient-distal end.

BRIEF DESCRIPTION OF THE DRAWINGS

FIG. 1 is an overview representation with essential function units of a device to reduce the electromagnetic field load in accordance with the invention.

FIG. 2 schematically illustrates a combined measurement and injection device in accordance with the invention.

DESCRIPTION OF THE PREFERRED EMBODIMENTS

FIG. 1 schematically shows a magnetic resonance apparatus wherein a patient 4 is supported for positioning of a guide wire 6. The patient-proximal end 10 of the guide wire 6 is located in the imaging region 12 of the magnetic resonance apparatus 2. Displacements of the end 10 can therefore be tracked in real time by means of magnetic resonance imaging.

The magnetic resonance apparatus 2 furthermore has a radio-frequency (RF) transmission resonator 14 that generates radio-frequency magnetic fields to excite the magnetic resonance in the imaging region 12. The radio-frequency transmission resonator 14 is activated by a radio-frequency transmitter 16 that is in turn connected with a radio-frequency oscillator 18. The signal generated by the radio-frequency oscillator 18 is modulated in amplitude and phase in the radio-frequency transmitter 16 and amplified to the required power level.

The electromagnetic fields generated by the radio-frequency transmission resonator 14 induce unwanted electrical currents in the guide wire 6 that can vary significantly depending on the geometric and electrical relationships. In the disadvantageous case, standing waves are induced on the guide wire 6.

A compensation device 20 is provided to compensate the standing waves generated in the guide wire 6 by the radio-frequency transmission resonator 14. The compensation device 20 comprises a control device 22 with a radio-frequency input 24 and a radio-frequency output 26. An injection device 28 that is fashioned to inject the radio-frequency power delivered by the control device 22 into the guide wire 6 is connected with the radio-frequency output 26.

A measurement device 30 is provided to measure an electrical variable that characterizes the standing wave on the guide wire. For precise detection of the electrical variable characterizing the standing wave, the measurement device 30 has two measurement sensors 32 and 34 arranged in the longitudinal direction of the guide wire 6. The electrical variable is therefore measured simultaneously at multiple points at the intervention apparatus 6, whereby the distribution of the electrical variable on the intervention apparatus 6 can be reconstructed well.

The measurement sensors 32 and 34 are connected with the measurement input or real value input of a regulator 36 that to which the value zero is provided as a desired value. The regulator 36 possesses two regulator outputs: a first regulator output is connected with an amplitude adjuster 38 and a second regulator output is connected with a phase adjuster 40. The amplitude adjuster 38 and the phase adjuster 40 modulate the signal delivered at the input 24 of the radio-frequency oscillator in terms of its amplitude and phase so that it largely compensates or compensates as much as possible the standing wave on the guide wire 6 after the amplification of said signal with an amplifier 42.

FIG. 2 shows an exemplary embodiment of a mechanical design of the compensation device. The control device 22 and the regulator 36 are accommodated in a first housing 44. The housing 44 possesses a radio-frequency input 24 and a radio-frequency output 26. Furthermore, a measurement value input 45 is also provided. The measurement device 30 with the two measurement value sensors 32 and 34 and the injection device 28 are arranged in a second housing 46. The spacing of the injection device 28 from the measurement device 30 that is required for the functionality determines the length of the housing 46. A tunnel 48 whose cross section is adapted to the external dimensions of the intervention apparatus is located in the longitudinal direction of the housing 46. In the present case of the guide wire 6, the diameter is in the millimeter range. The combined measurement value and injection device is freely movable in the longitudinal direction of the intervention apparatus 6.

Both the measurement device 30 and the injection device 28 are not in direct electrical contact with the guide wire 6. They operating inductively or capacitively in order to acquire the measurement values and to feed the compensation signal into the guide wire 6.

Although modifications and changes may be suggested by those skilled in the art, it is the intention of the inventors to embody within the patent warranted hereon all changes and modifications as reasonably and properly come within the scope of their contribution to the art.

We claim as our invention:

1. In a magnetic resonance (MR) apparatus comprising a radiofrequency (RF) transmitter connected with an RF oscillator and configured to radiate RF signals that excite nuclear spins in a subject located in an MR data acquisition volume of the MR apparatus, and an interventional device having at least a portion thereof located in said MR acquisition region and the interventional device being configured to interact with the subject during radiation of said RF signals, the improvement of a compensation device comprising:

a control device having an RF input and an RF output, said RF input being configured for connection with said RF oscillator;

an RF power injection device connected to said RF output of said control device, said RF power injection device being configured to inject RF power delivered by said control device into said interventional apparatus;

a measurement device configured to measure at least one electrical variable at said interventional device, said electrical variable changing dependent on said RF signals radiated by said RF transmitter; and a regulator connected to said control device and to said measurement device, said regulator being configured to adjust said control device to adjust delivery of said RF power in order to reduce said electrical variable at said interventional apparatus and, by reducing said electrical variable, said regulator also reducing an electromagnetic field load on the subject caused by interaction of the interventional device in the subject with the radiated RF signals.

2. A compensation device as claimed in claim 1 wherein said control device comprises an amplitude adjuster.

3. A compensation device as claimed in claim 1 wherein said control device comprises a phase adjuster.

4. A compensation device as claimed in claim 1 wherein said measurement device is configured to make a contact-free measurement of said electrical variable.

5. A compensation device as claimed in claim 1 wherein said measurement device is configured to measure radio-frequency current at said intervention apparatus as said electrical variable.

6. A compensation device as claimed in claim 1 wherein said measurement device is configured to measure said electrical variable at multiple, different points at said intervention apparatus.

7. A compensation device as claimed in claim 1 wherein said injection device is configured for contact-free injection of said radio-frequency power into said intervention apparatus.

8. A compensation device as claimed in claim 1 wherein said injection device is configured for capacitive injection of said radio-frequency power into said intervention apparatus.

9. A compensation device as claimed in claim 1 wherein said injection device is configured for inductive injection of said radio-frequency power into said intervention apparatus.

10. A compensation device as claimed in claim 1 wherein said measurement device and said injection device form a single structural unit, said structural unit comprising a tunnel therethrough that receives said intervention device therein.

11. A compensation device as claimed in claim 1 wherein said measurement device is configured to measure, as said at least one electrical variable, an electrical variable that presents a risk to the subject located in the data acquisition volume of said magnetic resonance apparatus.

12. A compensation device as claimed in claim 1 wherein said interaction of said interventional device in said subject with the radiated RF signals produces a standing wave on the interventional device in the subject, and wherein said regulator is configured to adjust said control device to adjust delivery of said RF power in order to substantially eliminate said standing wave.

* * * * *